US010602921B2

(12) United States Patent
Jensen

(10) Patent No.: US 10,602,921 B2
(45) Date of Patent: Mar. 31, 2020

(54) VIRTUAL DENTAL OPERATORY

(75) Inventor: Steven D. Jensen, South Jordan, UT (US)

(73) Assignee: CAO Group, Inc., West Jordan, UT (US)

(*) Notice: Subject to any disclaimer, the term of this patent is extended or adjusted under 35 U.S.C. 154(b) by 29 days.

(21) Appl. No.: 13/158,067

(22) Filed: Jun. 10, 2011

(65) Prior Publication Data

US 2011/0306005 A1     Dec. 15, 2011

Related U.S. Application Data

(60) Provisional application No. 61/353,614, filed on Jun. 10, 2010.

(51) Int. Cl.
*A61B 1/24* (2006.01)
*A61B 6/00* (2006.01)
*A61B 6/14* (2006.01)

(52) U.S. Cl.
CPC ............... *A61B 1/24* (2013.01); *A61B 6/14* (2013.01); *A61B 6/461* (2013.01); *A61B 6/486* (2013.01); *A61B 6/563* (2013.01)

(58) Field of Classification Search
CPC .. A61B 1/24; A61B 6/461; A61B 6/14; A61B 6/486; A61B 6/563
USPC ................ 348/66; 701/35; 386/282; 433/29
See application file for complete search history.

(56) References Cited

U.S. PATENT DOCUMENTS

| | | | | |
|---|---|---|---|---|
| 5,986,662 A | * | 11/1999 | Argiro | G06T 11/00 345/419 |
| 2006/0001740 A1 | * | 1/2006 | Fujie | A61B 1/00048 348/66 |
| 2006/0175477 A1 | * | 8/2006 | Parsons | A61G 15/10 248/125.7 |
| 2006/0256193 A1 | * | 11/2006 | Liu | A61B 1/00041 348/66 |
| 2008/0147267 A1 | * | 6/2008 | Plante | G07C 5/008 701/33.4 |

* cited by examiner

*Primary Examiner* — Tsion B Owens
*Assistant Examiner* — Berteau Joisil

(57) ABSTRACT

Embodiments of the present invention include methods, devices, and systems that light and magnify a treatment site within the oral cavity without interfering with a dental treatment procedure. In particular, example embodiments of the present invention provide a virtual operatory system that includes an image capture subsystem connected to an image display subsystem. For example, the image capture subsystem can capture and communicate a live image of a treatment site to the image display subsystem for the dental professional to view while performing a dental treatment procedure. In at least one example embodiment, the virtual operatory system can also include an image rendering subsystem that can render the live image of the treatment site in one or more ways to provide an improved visual to the dental professional of the treatment site.

13 Claims, 7 Drawing Sheets

VIRTUAL DENTAL OPERATORY

CROSS-REFERENCE TO RELATED APPLICATIONS

This application claims the benefit of U.S. Provisional Patent Application No. 61/353,614, filed Jun. 10, 2010, the content of which is incorporated herein by reference in its entirety.

TECHNICAL FIELD OF THE INVENTION

The present invention relates to the field of dental operatory and more particularly relates to devices, systems and methods of providing virtual live views of a treatment site.

BACKGROUND OF THE INVENTION

The modern dental operatory is centered on an adjustable dental chair. The dental chair has the purpose of providing the patient with a comfortable seat while at the same time allowing the dental professional to maneuver the dental chair in multiple directions to provide easier access to the patient's oral cavity. For example, a dental professional can recline, rise, lower, or spin the dental chair in order to maneuver the patient to allow the dental professional the best access to the patient's oral cavity to perform dental treatment procedures.

Although the dental chair can assist the dental professional in gaining access to the patient's oral cavity, the oral cavity is generally a small area in which it is difficult to perform dental treatment procedures. For example, dental treatment procedures usually include performing high tolerance procedures on a very small scale. Due to the high tolerances and small scale of most dental treatment procedures, dental professionals usually try to use some form of magnification to enhance their ability to perform the dental treatment procedure. The nature of the dental cavity, however, often makes it very difficult for a dental professional to use magnification tools effectively. For example, many dental professionals may use magnification lenses that may attach to a pair of conventional glasses and are hand adjustable. The magnification lenses, however, are usually heavy and are an annoyance when worn for long periods of time In addition to the small scale of dental treatment procedures, the oral cavity is generally a dark area, which further increases the challenges associated with performing dental treatment procedures. In particular, most dental professionals now use a high-powered overhead light to flood the oral cavity with light to help the dental professional adequately see the treatment site. Although the high-powered lights help provide light within the oral cavity, many time the dental professional's hands or tools block the light, thus limiting the effectiveness of the high-powered light.

What is needed in the art are systems, devices and methods that easily allow a dental professional to light and magnify a treatment site within the oral cavity without interfering with the dental treatment procedure.

SUMMARY OF THE INVENTION

Embodiments of the present invention include methods, devices, and systems that light and magnify a treatment site within the oral cavity without interfering with a dental treatment procedure. In particular, example embodiments of the present invention provide a virtual operatory system that includes an image capture subsystem connected to an image display subsystem. For example, the image capture subsystem can capture and communicate a live image of a treatment site to the image display subsystem for the dental professional to view while performing a dental treatment procedure. In at least one example embodiment, the virtual operatory system can also include an image rendering subsystem that can render the live image of the treatment site in one or more ways to provide an improved visual to the dental professional of the treatment site.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific example implementations thereof which are illustrated in the appended drawings. Understanding that these drawings depict only typical implementations of the invention and are not therefore to be considered to be limiting of its scope, the invention will be described and explained with additional specificity and detail through the use of the accompanying drawings in which.

DETAILED DESCRIPTION OF THE INVENTION

Embodiments of the present invention include methods, devices, and systems that light and magnify a treatment site within the oral cavity without interfering with a dental treatment procedure. In particular, example embodiments of the present invention provide a virtual operatory system that includes an image capture subsystem connected to an image display subsystem. For example, the image capture subsystem can capture and communicate a live image of a treatment site to the image display subsystem for the dental professional to view while performing a dental treatment procedure. In at least one example embodiment, the virtual operatory system can also include an image rendering subsystem that can render the live image of the treatment site in one or more ways to provide an improved visual to the dental professional of the treatment site.

As will be further explained below, the virtual dental operatory system allows the treatment site located within an oral cavity of a patient to be magnified without having to use heavy bulky optical magnifiers that are often uncomfortable to wear. Moreover, the virtual dental operatory system can provide an image where the treatment site is lighted well, or at least where the image of the treatment site is rendered such that the treatment site appears lighted. Furthermore, the virtual dental operatory system is configured such that the dental professional can perform the procedure minimizing the opportunity for the dental professional or the dental professional's tools to block the lighting effect.

Figure 1:
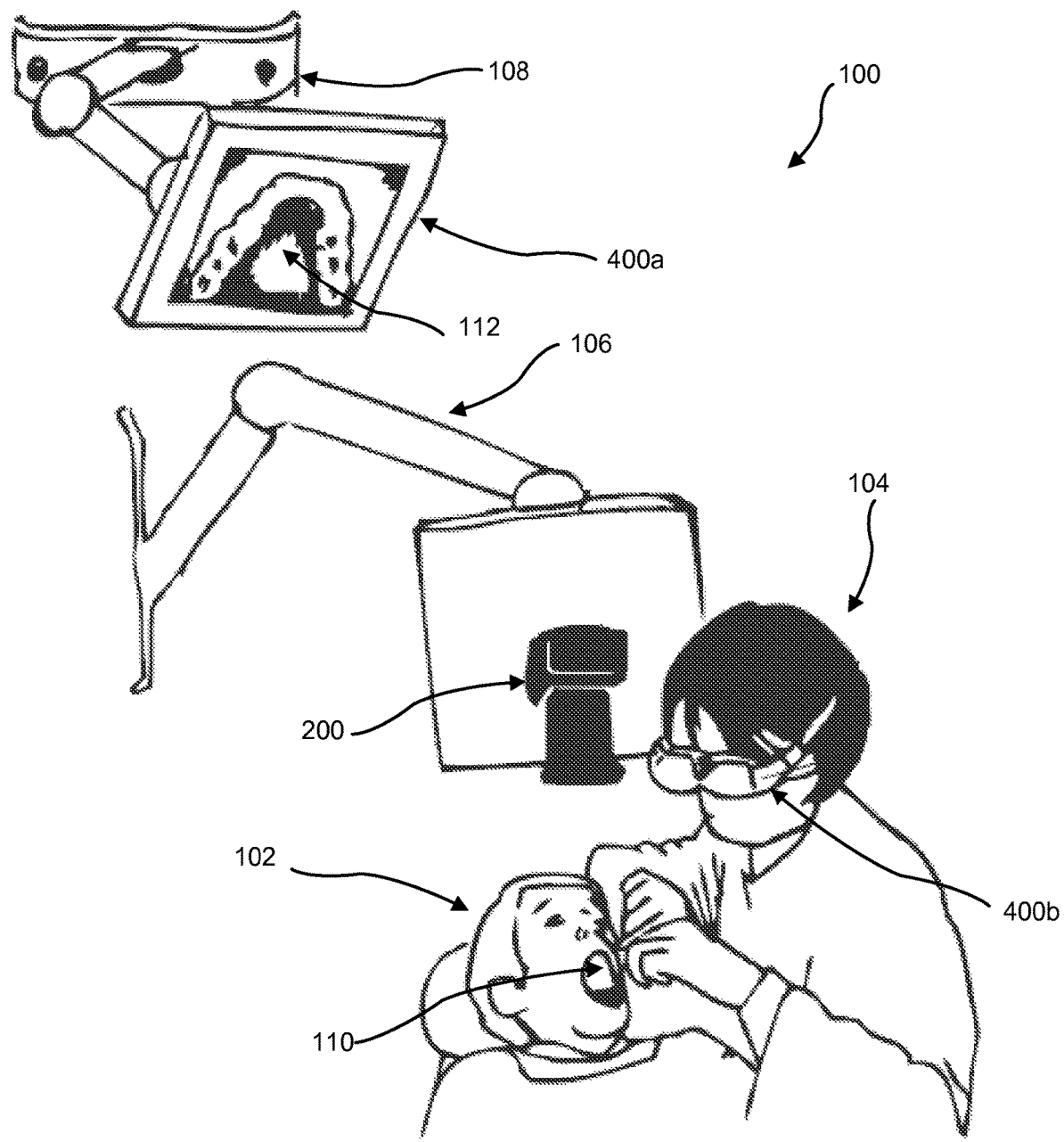
FIG. 1 illustrates various exemplary devices and components of a virtual dental operatory system.

FIG. 1 illustrates one example embodiment of a virtual dental operatory system 100. As used herein, operatory means any dental procedure, including but not limited to removal of cavity, adding fillings, root canals, bridges, orthodontics, surgery, and/or any or all treatments that take place around or within the oral cavity. As illustrated in FIG. 1, the virtual dental operatory system 100 can be arranged and configured to cooperate with a standard dental chair wherein a patient 102 sits while a dental professional 104 performs a dental treatment procedure. Although FIG. 1 illustrates one arrangement, the virtual dental operatory system 100 can be arranged in almost any arrangement as will be described further below.

Figure one illustrates that the virtual dental operatory system 100 can include an image capture subsystem 200. As illustrated in FIG. 1, the image capture subsystem 200 is configured to capture an image of a treatment site and communicate that image to various other subsystems within the virtual dental operatory system 100. In particular, the image capture subsystem 200 can be configured to capture and communicate a live video image of a treatment site.

As illustrated in FIG. 1, portions of the image capture subsystem 200 can be mounted to a wall or ceiling by way of an adjustable mounting system 106 that allows the dental professional 104 to position the image capture subsystem 200 in the best location to capture the best image. In alternative embodiments, portions of the image capture subsystem 200 can be located directly on dental tools that the dental professional is using, for example, a dental drill housing or similar dental tool. Alternatively, portions of the image capture subsystem 200 can be a free standing hand held tool that a dental assistant can maneuver and position while the dental professional 104 performs a dental treatment procedure.

As shown in FIG. 1, the image capture subsystem can capture an image of at least a portion of the patient's 102 oral cavity 110. The image capture subsystem can then communicate the image of the oral cavity 110 to an image display subsystem 400a and/or 400b such that the dental professional can view the image during the dental procedure. For example, FIG. 1 illustrates that that part of the image display subsystem 400a and/or 400b may include a monitor that is mounted to a wall or ceiling by way of an adjustable mounting system 108 that allows the dental professional to maneuver the monitor to almost any position or location. As illustrated, the monitor can display a virtual view 112 of the treatment site within the oral cavity 110. In an alternative, or in the same embodiment, the image display subsystem 400a and/or 400b can include goggles that include a display that allows the dental professional 104 to view the virtual view 112 of the treatment site within the oral cavity by wearing the goggles. These and other components will be explained in more detail below with reference to FIGS. 2 through 5.

Figure 2:
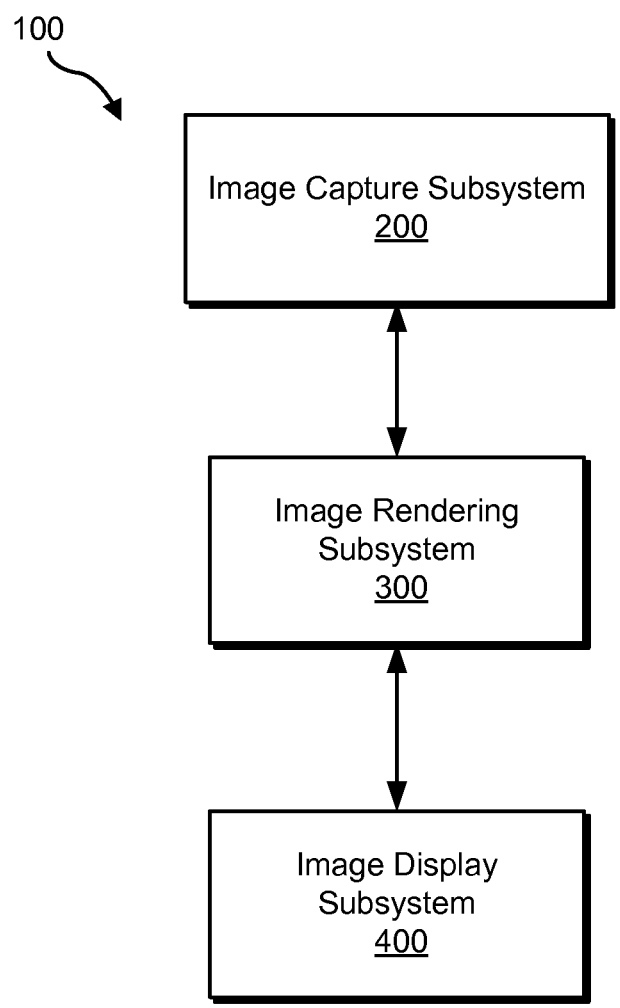
FIG. 2 illustrates an exemplary implementation of the system of FIG. 1 according to principles described herein.

In addition to the various example components and subsystems illustrated in FIG. 1, FIG. 2 further illustrates an example embodiment of the virtual dental operatory system 100. As discussed above with reference to FIG. 1, the virtual dental operatory system 100 can include the image capture subsystem 200 that can capture an image of a treatment area within a patient's oral cavity to produce a captured image.

As illustrated in FIG. 2, the image capture subsystem 200 can be communicably connected to an image rendering subsystem 300. The image capture subsystem 200 can communicate the captured image to the image rendering subsystem 300. After receiving the captured image, the image rendering subsystem 300 can apply one or more rendering routines to the captured image to produce a rendered image.

As further illustrated in FIG. 2, the image rendering subsystem 300 can be communicably connected to an image display subsystem 400. In particular, the image rendering subsystem 300 can communicate the rendered image to the image display subsystem 400. After receiving the rendered image, the image display subsystem 400 can display the rendered image on one or more image display devices.

The image capture subsystem 200, the image rendering subsystem 300 and the image display subsystem 400 (the "subsystems") can communicate using any suitable communication technologies, devices, networks, media, and protocols supportive of remote data communications. For example, the subsystems can communicate over a network using any communication platforms and technologies suitable for transporting captured images and/or communication signals, including known communication technologies, devices, transmission media, and protocols supportive of remote data communications, examples of which include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Evolution Data Optimized Protocol ("EVDO"), Time Division Multiple Access ("TDMA") technologies, radio frequency ("RF") signaling technologies, wireless communication technologies (e.g., Bluetooth, Wi-Fi, etc.), optical transport and signaling technologies, live transmission technologies (e.g., media streaming technologies), media file transfer technologies, in-band and out-of-band signaling technologies, and other suitable communications technologies.

Moreover, the network may include one or more networks or types of networks (and communication links thereto) capable of carrying communications, captured images, and/or data signals between the subsystems. For example, the network may include, but is not limited to, one or more wireless networks, cable networks, hybrid fiber coax networks, optical fiber networks, broadband networks, narrowband networks, the Internet, wide area networks, local area networks, public networks, private networks, packet-switched networks, and any other networks capable of carrying data and/or communications signals between the subsystems. Communications between the subsystems may be transported using any one of above-listed networks, or any combination or sub-combination of the above-listed networks.

Figure 3:
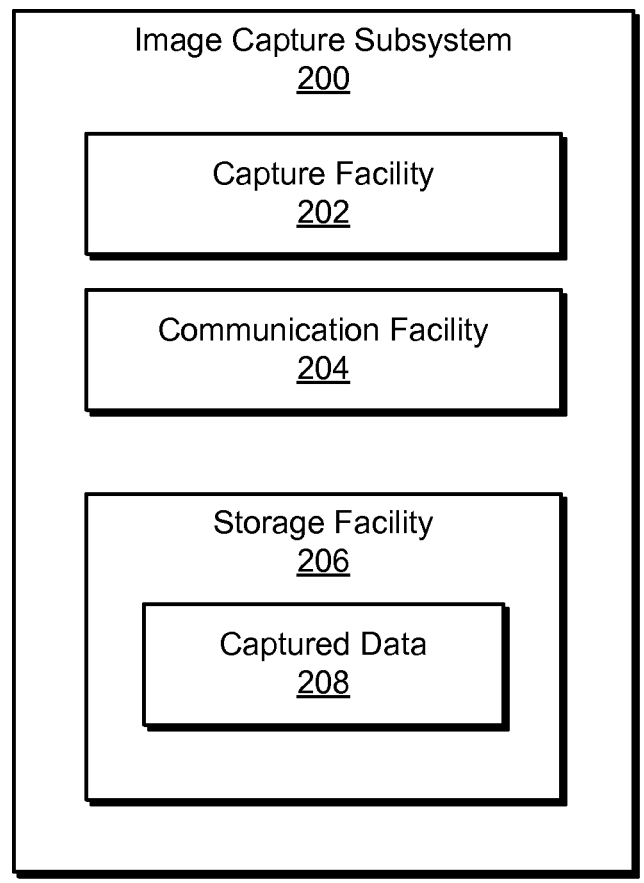
FIG. 3 illustrates exemplary components of an image capture subsystem according to principles described herein.

The various subsystems illustrated in FIGS. 1 and 2 can each include various facilities that assist the various subsystems in performing various tasks within the virtual dental operatory system 100. For example, FIG. 3 illustrates on example of the image capture subsystem 200. As illustrated, the image capture subsystem 200 can include a capture facility 202. The capture facility 202 can include any devices that provide for the capture of an image, and in particular, the capture of a live video image.

For example, the capture facility 202 can include a camera. In one embodiment, the camera can be a live feed auto-focus camera. The camera can have various optical magnification lenses to provide optical magnification of the treatment site. For example, a camera such as the SONY ALPHA A350 is a camera with live feed and auto focus capabilities.

The capture facility can be configured to focus on a particular instrument such that the camera's focus automatically adjusts depending on the location of the particular instrument within the oral cavity. This feature can be provided by image recognition routines that are part of the capture facility 202.

The image capture subsystem 200 can further include a communication facility 204. Communication facility 204 may be configured to facilitate communication between the image capture subsystem and the image rendering subsystem 300 and/or the image display subsystem 400. In particular, communication facility 204 may be configured to transmit and/or receive communication signals, captured images, metadata and/or any other data to/from the image capture subsystem 200. For example, communication facility 204 may transmit data representative of one or more captured images to the image rendering subsystem 300.

Data representative of captured images may be transmitted in one or more media content streams, as one or more data files, or in any other suitable manner as may serve a particular implementation. Communication facility 204 may be configured to interface with any suitable communication media, protocols, and formats, including any of those mentioned above.

In addition to the communication facility 204, the image capture subsystem 200 can include a storage facility 206. Storage facility 206 may be configured to maintain captured data 208 representative of one or more captured images. It will be recognized that storage facility 208 may maintain additional or alternative data as may serve a particular implementation. In one example, the captured data can be used by the dentist to demonstrate a particular procedure to another patient, insurance company, or keep it on file for other purposes, such as if a particular procedure fails then the dentist can review the procedure in an attempt to identify the cause of failure.

Figure 4:
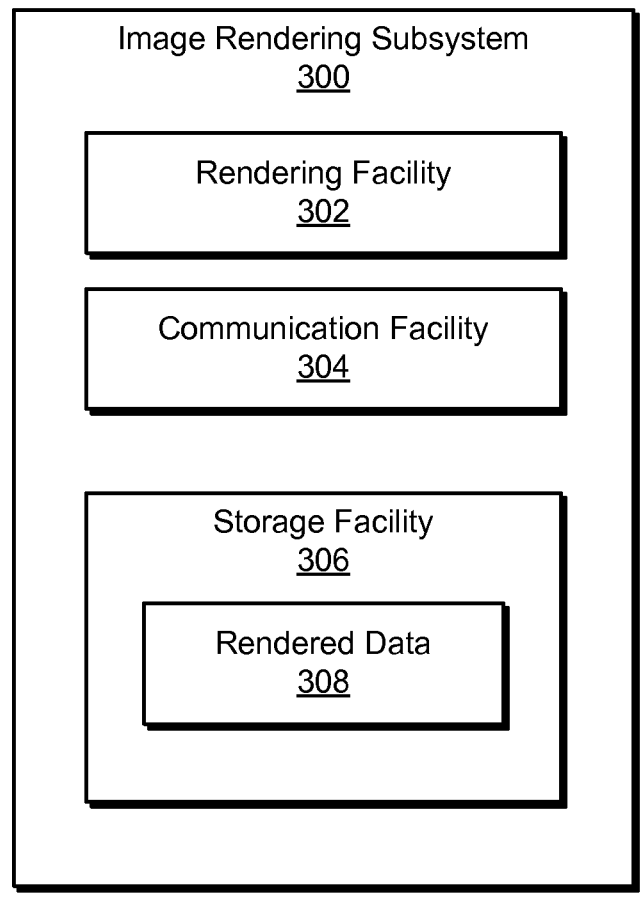
FIG. 4 illustrates exemplary components of an image rendering subsystem according to principles described herein.

FIG. 4 illustrates an example embodiment of the image rendering subsystem 300. The image rendering subsystem 300 can include a rendering facility 302 configured to perform one or more rendering routines on the captured image. The rendering routines can perform digital enhancements that render or change the captured image to a rendered image. The rendering or changes to the captured image can enhance the captured image in one or more ways such that resulting rendered image allows the dental professional a superior view or visual access to the treatment site.

For example, rendering routines performed on the captured image can magnify, brighten, increase/decrease contrast, enlarge, zoom in, zoom out, provide a three-dimension model, change colors, add lighting effects and/or change or render the captured image in any way to produce a customized rendered image for the dental professionals use.

The image rendering subsystem 300 can include a user input interface that allows the dental professional to customize the rendered image by inputting rendering specifications. The rendering facility can be provided with pre-set rendering routines that easily allow the dental professional to render the captured image in a preset way and also be able to switch back and forth between two or more pre-set rendering routines during a procedure.

The image rendering subsystem 300 can further include a communication facility 304. Communication facility 304 may be configured to facilitate communication between the image rendering subsystem 300 and the image capture subsystem 200 and/or the image display subsystem 400. In particular, communication facility 304 may be configured to transmit and/or receive communication signals, captured images, metadata and/or any other data to/from the image rendering subsystem 300. For example, communication facility 304 may transmit data representative of one or more rendered images to the image display subsystem 400.

Data representative of rendered images may be transmitted in one or more media content streams, as one or more data files, or in any other suitable manner as may serve a particular implementation. Communication facility 304 may be configured to interface with any suitable communication media, protocols, and formats, including any of those mentioned above.

In addition to the communication facility 304, the image rendering subsystem 300 can include a storage facility 306. Storage facility 306 may be configured to maintain rendered data 308 representative of one or more rendered images. It will be recognized that storage facility 308 may maintain additional or alternative data as may serve a particular implementation. In one example, the rendered data 308 can be used by the dentist to demonstrate a particular procedure to another patient, insurance company, or keep it on file for other purposes, such as if a particular procedure fails then the dentist can review the rendered data in an attempt to identify the cause of failure.

Figure 5:
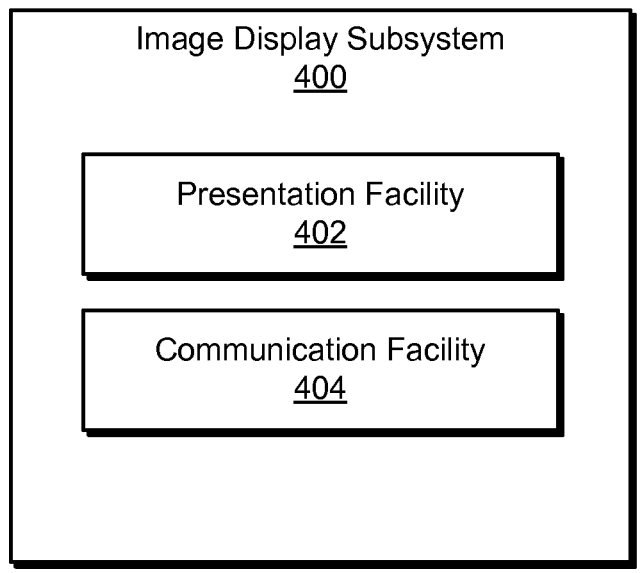
FIG. 5 illustrates exemplary components of an image display subsystem according to principles described herein.

FIG. 5 illustrates an example embodiment of the image display subsystem 400. For example, the image display subsystem 400 can include a presentation facility 402. The presentation facility has the ability to use data received from either the image capture subsystem 200 or the image rendering subsystem 300 and create a visual depiction of the treatment site.

For example, the presentation facility 400 can include a monitor or projector that displays a visual depiction of the treatment site. In another example, the presentation facility 400 can include goggles (e.g., virtual reality goggles) that are capable of producing a visual depiction of the treatment site to the wearer of the goggles. In one embodiment, the goggles can be TECHWOOD TG-06V IC Goggles from WELTON ELECTRONICS. The goggles can be worn like traditional glasses or goggles with the depiction of the treatment site viewed directly through the goggles.

With the goggles, or the monitor, the dental professional can perform a dental procedure on the patient, while directly monitoring an enhanced view of the dental procedure through the virtual operatory system 100. Thus, the dental professional is provided with a superior view of the oral cavity during the procedure (including magnification and lighting effects).

The image display subsystem 400 can further include a communication facility 404. Communication facility 404 may be configured to facilitate communication between the image display subsystem 400 and the image capture subsystem 200 and/or the image rendering subsystem 300. In particular, communication facility 404 may be configured to transmit and/or receive communication signals, captured images, rendered images, metadata and/or any other data to/from the image display subsystem 400. For example, communication facility 404 may receive data representative of one or more rendered images from the image rendering subsystem 300.

Data representative of rendered images may be transmitted in one or more media content streams, as one or more data files, or in any other suitable manner as may serve a particular implementation. Communication facility 404 may be configured to interface with any suitable communication media, protocols, and formats, including any of those mentioned above.

Figure 6:
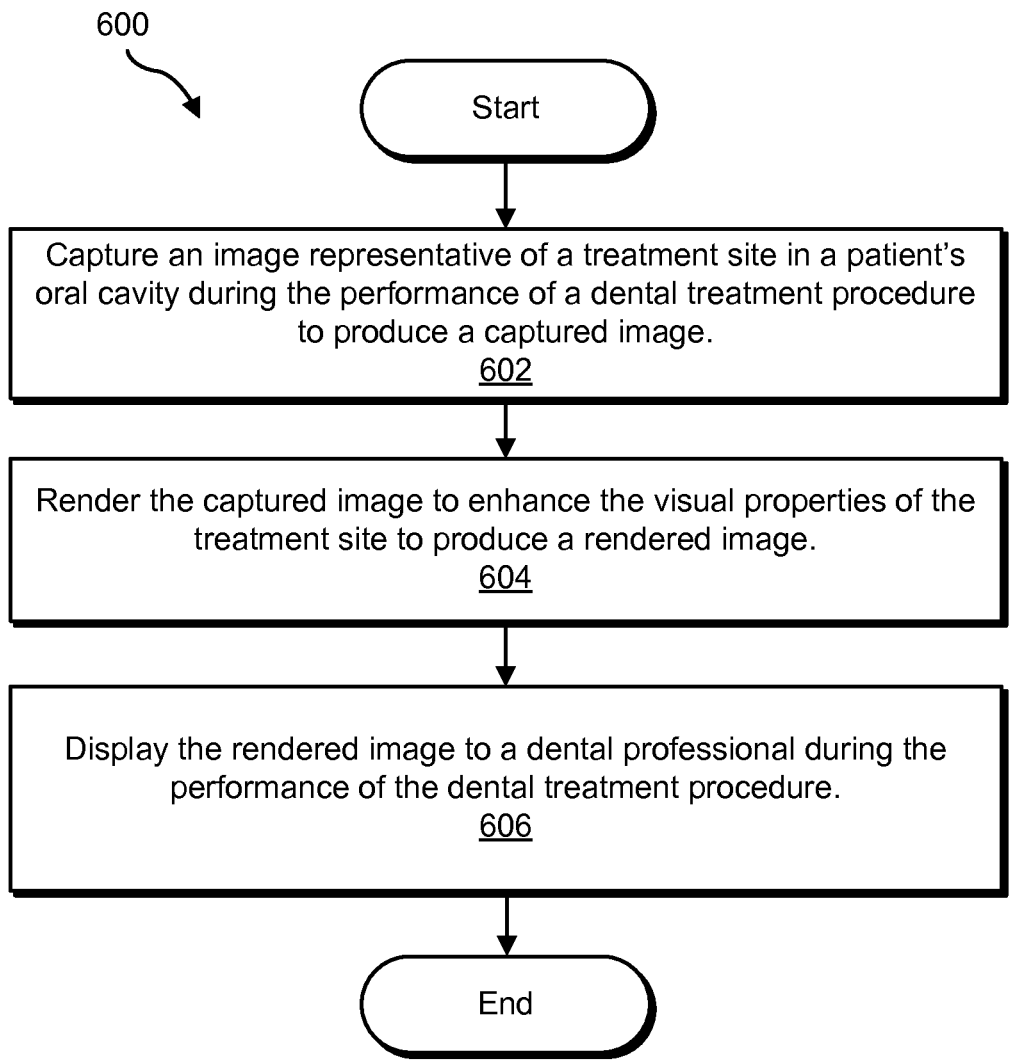
FIG. 6 illustrates an exemplary method of performing virtual dental operatory.

FIG. 6 illustrates an exemplary method 600 of virtual dental operatory. While FIG. 6 illustrates exemplary steps according to one embodiment, other embodiments may omit, add to, reorder, and/or modify any of the steps shown in FIG. 6. The steps shown in FIG. 6 may be performed by any component or combination of components of the virtual dental operatory system 100.

In step 602, an image representative of a treatment site in a patient's oral cavity is captured during the performance of a dental treatment procedure to produce a captured image. To illustrate, FIG. 3 illustrates that the image capture subsystem 200 can include the capture facility that is configured to capture an image of the treatment site. For example, a camera or similar image capturing device can be used to capture the image.

In step 604, the captured image is rendered to enhance the visual properties of treatment site to produce a rendered image. To illustrate, FIG. 4 illustrates that the image rendering subsystem 300 can include a rendering facility that is configured to apply one or more rendering routines to the captured image to produce a rendered image that is enhanced and customized to provide a superior visual depiction of the treatment site.

In step 606, the rendered image is displayed to the dental professional during the performance of the dental treatment procedure. To illustrate, FIG. 5 illustrates that the image display subsystem 400 can include a presentation facility that is configured to display the rendered image. For example, virtual reality goggles can be used to display the rendered image to the dental professional.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software), or combinations of computer-implemented instructions and hardware, configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer may read.

Figure 7:
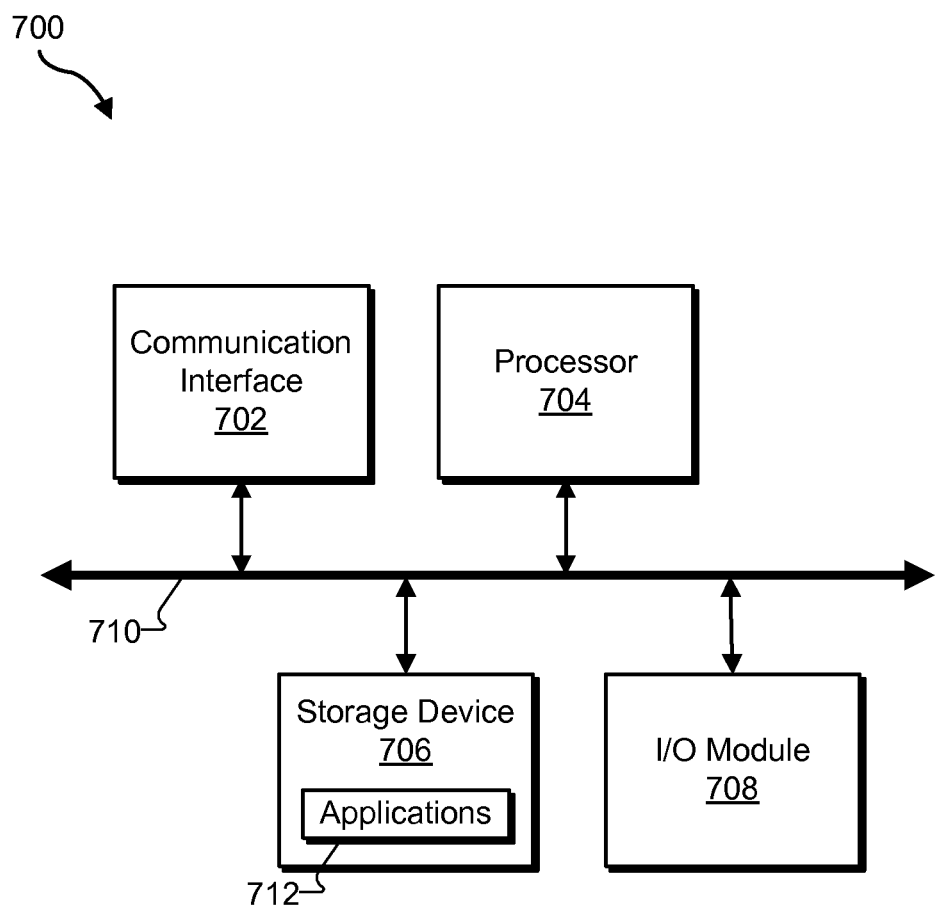
FIG. 7 illustrates an example computing device according to principles described herein.

FIG. 7 illustrates an exemplary computing device 700 that may be configured to perform one or more of the processes described herein. As shown in FIG. 7, computing device 700 may include a communication interface 702, a processor 704, a storage device 706, and an input/output ("I/O") module 708 communicatively connected via a communication infrastructure 710. While an exemplary computing device 700 is shown in FIG. 7, the components illustrated in FIG. 7 are not intended to be limiting. Additional or alternative components may be used in other embodiments. Components of computing device 700 shown in FIG. 7 will now be described in additional detail.

Communication interface 702 may be configured to communicate with one or more computing devices. Examples of communication interface 702 include, without limitation, a wired network interface (such as a network interface card), a wireless network interface (such as a wireless network interface card), a modem, and any other suitable interface. In at least one embodiment, communication interface 702 may provide a direct connection between system 100 and one or more of provisioning systems via a direct link to a network, such as the Internet. Communication interface 702 may additionally or alternatively provide such a connection through, for example, a local area network (such as an Ethernet network), a personal area network, a telephone or cable network, a satellite data connection, a dedicated URL, or any other suitable connection. Communication interface 702 may be configured to interface with any suitable communication media, protocols, and formats, including any of those mentioned above.

Processor 704 generally represents any type or form of processing unit capable of processing data or interpreting, executing, and/or directing execution of one or more of the instructions, processes, and/or operations described herein. Processor 704 may direct execution of operations in accordance with one or more applications 712 or other computer-executable instructions such as may be stored in storage device 706 or another computer-readable medium.

Storage device 706 may include one or more data storage media, devices, or configurations and may employ any type, form, and combination of data storage media and/or device. For example, storage device 706 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 706. For example, data representative of one or more executable applications 712 (which may include, but are not limited to, one or more of the software applications described herein) configured to direct processor 704 to perform any of the operations described herein may be stored within storage device 706. In some examples, data may be arranged in one or more databases residing within storage device 706.

I/O module 708 may be configured to receive user input and provide user output and may include any hardware, firmware, software, or combination thereof supportive of input and output capabilities. For example, I/O module 708 may include hardware and/or software for capturing user input, including, but not limited to, a keyboard or keypad, a touch screen component (e.g., touch screen display), a receiver (e.g., an RF or infrared receiver), and/or one or more input buttons.

I/O module 708 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 708 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 700. For example, one or more applications 712 residing within storage device 706 may be configured to direct processor 704 to perform one or more processes or functions associated with capture facility 202, communication facility 204, rendering facility 302, communication facility 304, presentation facility 402, and/or communication facility 404. Likewise, storage facilities 206 and/or 306 may be implemented by or within storage device 706.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A virtual dental operatory system, comprising:
    a capture facility configured to capture an image of a treatment site within a patient's oral cavity resulting in a captured image, wherein at least a portion of the capture facility is located on a hand held tool;
    a rendering facility communicatively coupled to the capture facility and configured to:
        receive the captured image; and
        apply one or more rendering routines to the captured image resulting in a rendered image; and
    wherein the rendering facility is provided with preset rendering routines that easily allow a dental professional to render the captured image in a preset way and also be able to switch back and forth between two or more preset rendering routines during a procedure;
    a presentation facility comprising virtual reality goggles communicatively coupled to the rendering facility and configured to display the rendered image to a dental professional while performing a dental procedure, and
    wherein, the rendered image represents a live view of the treatment site during the dental procedure.

2. The system recited in claim 1, wherein the capture facility includes a camera.

3. The system recited in claim 2, wherein the camera is an autofocus camera.

4. The system recited in claim 3, wherein the camera has a variety of optical magnification.

5. The system recited in claim 1, wherein the one or more rendering routines applied to the captured image include adding a lighting effect.

6. The system recited in claim 4, wherein the one or more rendering routines applied to the captured image include adding a magnification effect.

7. The system recited in claim 4, wherein the one or more rendering routines applied to the captured image include selecting a portion of the captured image focusing on the selected portion.

8. The system recited in claim 1, wherein the presentation facility includes a monitor that displays the rendered image.

9. A method comprising:
    capturing an image representative of a treatment site in a patient's oral cavity with an image capture system wherein at least a portion of the image capture system is located directly on a dental tool that a dental professional is using during the performance of a dental treatment procedure to produce a captured image;
    rendering the captured image with preset rendering routines to enhance the visual properties of the treatment site to produce a rendered image and switching back and forth between two or more of the preset rendering routines during a procedure; and
    displaying the rendered image to the dental professional during the performance of the dental treatment procedure with virtual reality goggles.

10. The method recited in claim 9, wherein the capturing of the image is provided by a digital camera.

11. The method recited in claim 9, wherein the displaying of the rendered image is further provided by a monitor.

12. The method recited in claim 9, wherein the rendering the captured image includes adding lighting effects to the captured image.

13. The method recited in claim 9, wherein the rendering the captured image includes magnification of the captured image.

* * * * *